United States Patent
Janzen

[11] Patent Number: 6,126,674
[45] Date of Patent: Oct. 3, 2000

[54] SURGICAL SLIDING SHAFT INSTRUMENT

[75] Inventor: Peter Janzen, Tuttlingen, Germany

[73] Assignee: MediPlus Instruments GmbH U. Co. KG, Tuttlingen, Germany

[21] Appl. No.: 09/181,454

[22] Filed: Oct. 28, 1998

[30] Foreign Application Priority Data

Nov. 3, 1997 [DE] Germany .......................... 197 48 369

[51] Int. Cl.[7] .................................................. A61B 17/28
[52] U.S. Cl. ................................ 606/206; 606/208; 606/1
[58] Field of Search .................................... 606/205–210, 606/83, 1

[56] References Cited

U.S. PATENT DOCUMENTS

| | | | |
|---|---|---|---|
| 4,483,562 | 11/1984 | Schoolman | 128/321 |
| 5,176,702 | 1/1993 | Bales et al. | 606/208 |
| 5,318,589 | 6/1994 | Lichtman | 606/205 |
| 5,755,713 | 5/1998 | Bilof et al. | 606/1 |
| 5,851,214 | 12/1998 | Larsen et al. | 606/208 |

*Primary Examiner*—Gary Jackson
*Assistant Examiner*—Jonathan D. Goldberg
*Attorney, Agent, or Firm*—Foley, Hoag & Eliot, LLP

[57] ABSTRACT

The systems described herein include a surgical instrument having an elongate shaft member, a slide mounted thereon, a handle with two legs, a disengagement mechanism permitting the mounted slide to be removed from the elongate shaft member, and a lock mechanism preventing slide disengagement. In one embodiment, the handle comprises a first and a second handle leg, the second handle leg pivotable around the first handle leg, and the second handle leg having a proximal end bearing an axially directed slot that permits engagement with a cross-pin. In this embodiment, maximal spreading of the two handle legs inclines the slot in the proximal end of the second handle leg in a proximal direction, permitting the disengagement of the crosspin from the slot when the slide is retracted to its most proximal position. One embodiment of the apparatus described herein includes a lock mechanism comprising a mechanical stop that is capable of limiting the rotation of the second handle leg into a maximally spread position.

16 Claims, 3 Drawing Sheets

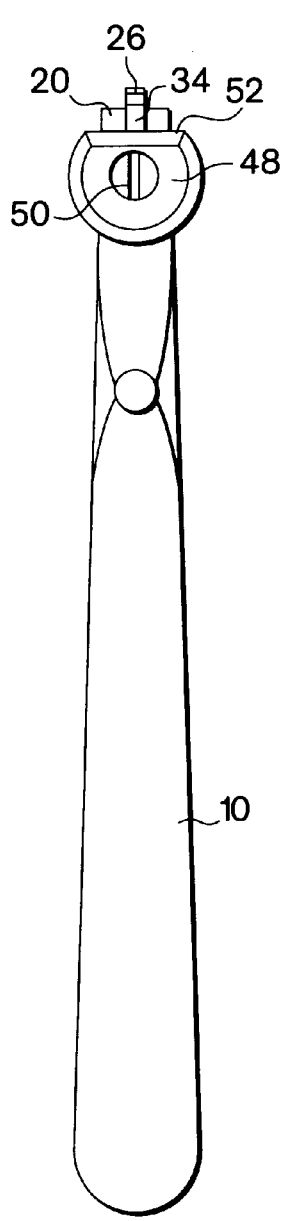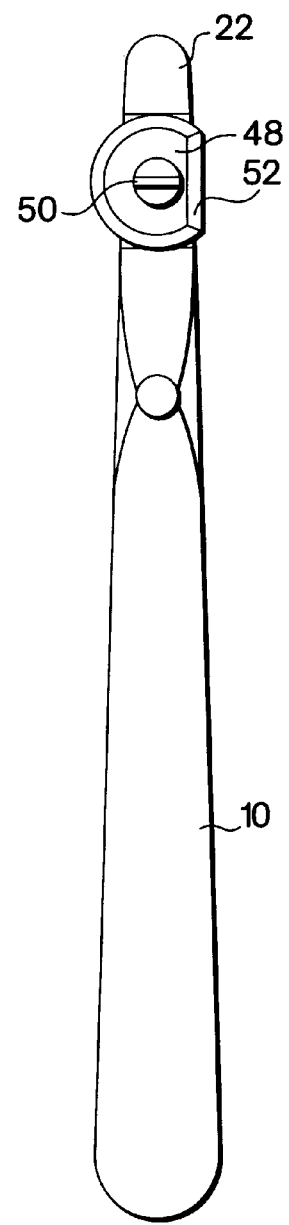

SURGICAL SLIDING SHAFT INSTRUMENT

BACKGROUND OF THE INVENTION

1. Field of the Invention

The invention relates to the field of surgical instruments. In particular, it relates to a surgical instrument for use in general and minimally invasive surgery.

2. Description of Related Art

It is advantageous in the field of general or minimally invasive surgery to perform operative interventions with an instrument that provides a proximal handle capable of being opened with one or with two hands and a distal tip that can be positioned and manipulated with precision. A surgical sliding shaft instrument is capable of being used in this manner. The sliding shaft apparatus of a surgical instrument permits the positioning and action of the distal tip to be effected by maneuvers of the proximal handle. A surgical sliding shaft instrument includes a slide that is axially displaceable on the shaft. Commonly, the slide can be displaced proximally and distally on the shaft by the operator's opening or closing the legs of a handle. This can allow the operator to control the placement of the distal tip of the shaft with the same hand that displaces the slide proximally or distally, although the instrument can also provide a handle best activated with two hands. The motion of the slide takes place as the legs of the handle pivot with respect to one another. As the slide moves proximally or distally, it may engage other parts of the surgical instrument and cause their displacement. For example, the sliding mechanism can actuate a mechanism for providing a punch biopsy, a mechanism that acts as a rongeur or a mechanism for grasping tissues or objects.

In order to clean and sterilize a surgical instrument consisting of several movable pieces, it is desirable that the instrument be capable of dissasembly. This allows each component to be cleaned and sterilized separately, so that each surface achieves maximum asepsis. In a sliding shaft instrument, such dissasembly can require the slide being separated from the shaft. An example of a sliding shaft instrument capable of disassembly is described in DE 4316768 A1. In the instrument described in this patent, the slide is mounted on the shaft by swallowtail guides. When the slide is displaced into a retracted position on the proximal portion of the shaft, the swallowtail guide is disengaged and the slide can be removed from the shaft. The shaft of this instrument is permanently connected to a first handle leg. The second pivotable handle leg is affixed to the slide. The second handle leg is held in place by a cross pin that engages an open-ended slot of the second handle leg. As long as the slide is affixed to the second handle leg by its cross pin, it cannot be moved into the proximal end position that would permit it to be separated from the shaft. In order to disassemble the sliding shaft instrument, the articulation pin connecting the two handle legs is pulled out, so that the handle legs are no longer connected with one another. The cross pin is then removed from the pivotable handle leg. This frees the slide, so it can be slid into its proximal end position. Once in this position, the swallowtail guide can be disengaged from the shaft. The instrument according to this patent comes apart in four pieces, permitting cleaning and sterilization of the component parts of the instrument. However, the disassembly and subsequent reassembly of the sliding shaft is time-consuming and cumbersome. Further, there is the risk of component parts getting lost. The articulation pin is particularly vulnerable to misplacement. Without this component, the device cannot be reassembled.

A sliding shaft instrument is described in DE 19513572 A1 in which a pivotable member is mounted on the proximal end of the slide and is brought into engagement for coupling with the pivotable handle leg. By pivoting this member outward, the coupling connection between the slide and the handle leg can be released. Once released, the slide can be moved into position on the proximal end of the shaft so that it can be separated from the shaft. In this instrument, the handle legs do not have to be separated from one another. The pivotable member and its lock are mechanically complex, however. This raises problems of adequate cleaning and sterilization, since the components cannot be fully detached.

Therefore, there remains in the art a need for a surgical sliding shaft instrument that permits easy cleaning and sterilization, without undue risk of loss of the components once disassembled. Furthermore, it is desirable that the device be mechanically simple, so that disassembly and reassembly is not unduly burdensome or time-consuming. A further desirable feature of the instrument is a slide that can be removed and reinstalled without further disassembly of the sliding shaft. It is also desirable to provide a control mechanism for a surgical device that allows precise placement of the distalmost portion of the shaft and precise control of the action of the sliding shaft.

SUMMARY OF THE INVENTION

According to the present invention, a surgical instrument includes an elongate shaft member, a slide axially displaceable on the shaft member, and a first and second handle leg, with the first handle leg positioned proximal to the second handle leg. In one embodiment, the second handle leg may be capable of pivoting around a connection to the first handle leg. In this embodiment, the second handle leg may further include a longitudinal slot in its proximal end that permits articulation with a crosspin positioned on the slide. The slide may be affixed to the shaft member in a slide path so that it remains attached during proximal and distal displacement. With maximal proximal retraction, the slide may disengage from the slide path. With the handle legs in their maximally spread position, the slot on the proximal end of the second handle leg may incline rearward, permitting the cross pin on the slide to be disengaged. Once the cross pin is disengaged and once the slide is disengaged from the slide path, the slide may be removed from the instrument for cleaning, sterilization, repair or alteration. In one embodiment, the slot may form form an acute angle to the direction of the axial displacement of the slide along the slide path so that the cross pin is displaced over the proximal lip of the slot. When the pivotable handle leg is in this maximally spread handle position, the cross pin end preferably may come completely free of the slot in the handle leg. The slide may then be removed from the shaft without it being necessary to take the handle apart.

In order to prevent the slide from moving into its proximal end position when the instrument is in use and thus coming loose from the shaft, a lock may be provided that limits the pivoting movement of the second handle in such fashion that this leg cannot be pivoted into the maximally spread handle position. As long as the lock is engaged, the second handle leg may not be pivoted to the point where the cross pin of the slide comes free from the handle leg. The slide may therefore also not be slid into its proximal end position in which it can be removed from the shaft.

If the instrument is to be taken apart for cleaning and sterilization, the lock may be released so that the second handle leg may be pivoted completely and releases the slide. To assemble the sliding shaft instrument, the slide may be slid onto the shaft with the lock released until its cross pin enters the slot of the pivotable handle leg. Then the handle leg may be pivoted in the closing direction until the lock can be engaged. With the lock in this position, the slide may be guided on the shaft without concern about inadvertent release of the slide from the slide path. In one embodiment, the lock may include a mechanical stop element that moves into the locking position and may be moved out of this locking position into the release position. Advantageously, the stop element may be locked at least in the locking position. In one embodiment, the lock may be made in the form of a latch so that the stop element is held stably in its locking position or release position, but may be adjusted simply by overcoming the latch. In one embodiment, the stop element may engage the pivotable handle leg in order to limit its pivoting movement. In an alternate embodiment, the stop element may intersect with the displacement path of the slide in order to prevent it from sliding into the proximally retracted end position. Since the handle leg is coupled with the slide by the cross pin, a lock engaging the slide may also limit the pivoting movement of the handle leg. The stop element may be made rotatable or pivotable in order to be turned or pivoted into the path of movement of the second handle leg or the slide. Likewise, a displaceable mounting of the stop element may be possible in order to slide it into the movement path or to slide it out of this path.

Many other features and advantages of the present invention will become apparent from the following description. A more comprehensive understanding of the systems described herein will be evident after reviewing the forthcoming diagrammatic representations and their detailed descriptions.

BRIEF DESCRIPTION OF THE DRAWINGS

The foregoing and other advantages of the invention will be appreciated more fully from the following description thereof, with reference to the accompanying drawings wherein:

FIG. 2 is a rear view of the sliding shaft instrument in the unlocked position with the slide removed.

FIG. 3 is a rear view of the sliding shaft instrument in the locked operating position.

DETAILED DESCRIPTION OF THE PREFERRED EMBODIMENT(S)

Figure 1:
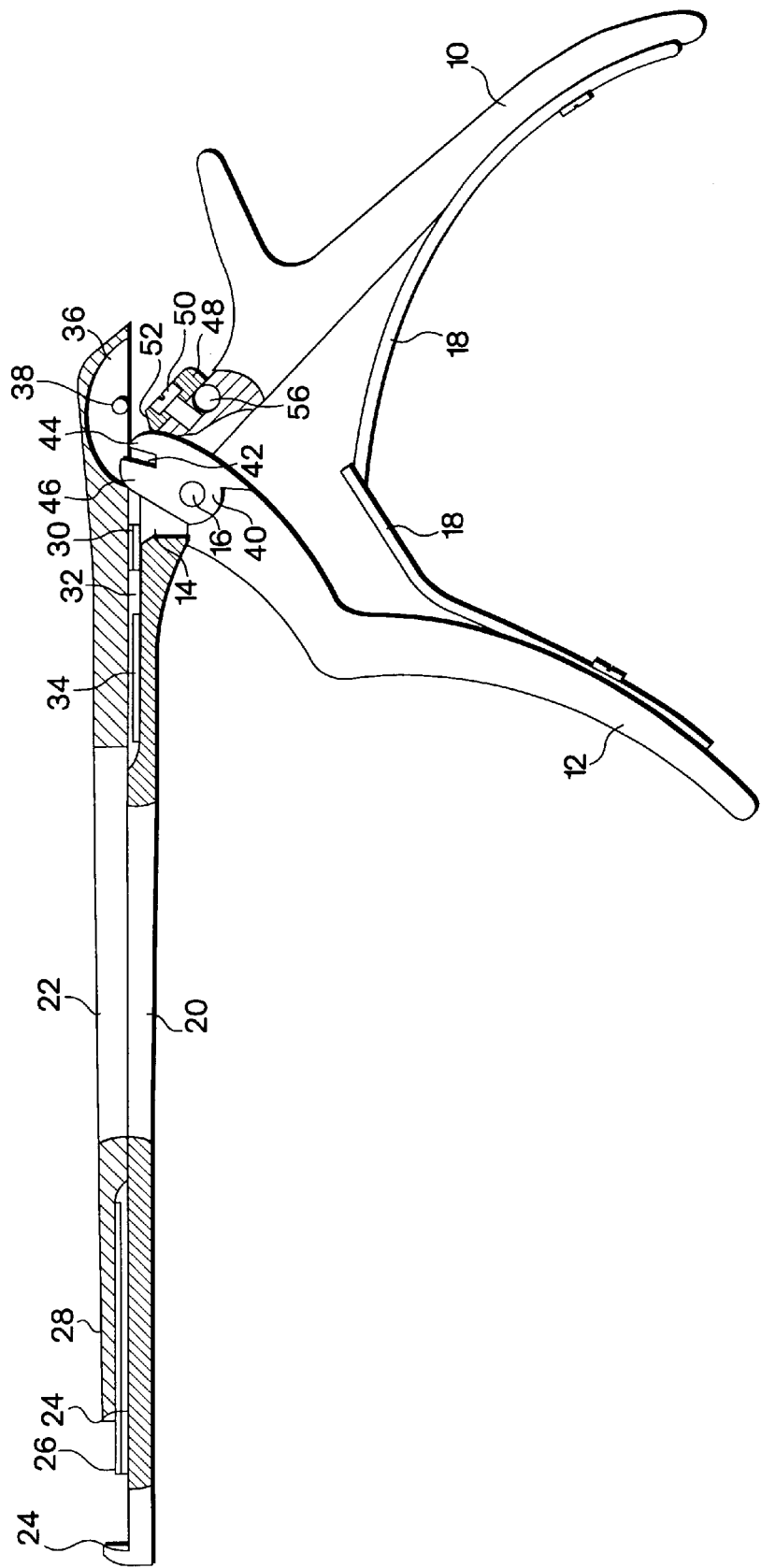
FIG. 1 shows a side view in partial axial section of the sliding shaft instrument in the unlocked position.

To provide an overall understanding of the invention, certain illustrative embodiments will now be described, including a sliding shaft surgical instrument. However, it will be understood by one of ordinary skill in the art that the surgical instrument systems described herein are merely illustrative of the invention, and that other systems can include the teachings discussed herein. Furthermore, it will be understood that the systems described herein can be adapted and modified without departing from the scope thereof Referring to FIG. 1, an embodiment of a surgical instrument of the present invention is shown. This embodiment includes a first handle leg 10, a second handle leg 12, shaft 20 and a slide 22. The component parts of the first handle leg 10 and the second handle leg 12 jointly form the handle of the device. The second handle leg 12 is intercalated into an axial opening 14 of the first handle leg 10 and is connected pivotably to the first handle leg 10 in the vicinity of this opening 14 by an articulation pin 16. Between handle legs 10 and 12, spreading springs 18 are inserted that spread handle legs 10 and 12 apart.

In one embodiment, a shaft 20 is shaped integrally as a distally projecting extension of the first handle leg 10, said shaft having an approximately semicircular cross-sectional profile with a flat top. On the top side of shaft 20, a slide 22 can be placed which likewise has an approximately semicircular cross-sectional profile. Shaft 20 and slide 22 abut one another with their flat profile sides and thus combine to form an approximate circle in cross section. Slide 22 extends substantially over the entire length of shaft 20. At the distal end of shaft 20 and slide 22, active parts 24 are provided which mesh with one another. In the embodiment shown, active parts 24 are the cutting edges of a punch. It is understood that other sorts of active parts 24 can be provided without departing from the scope of the systems described herein. Active parts 24 are familiar to those of ordinary skill in the art, including such devices as cutting mechanisms, grasping mechanisms, rongeur mechanisms, stapling mechanisms and hemostatic mechanisms. Other types of active parts 24 can be provided by those skilled in the relevant surgical arts.

Slide 22 is axially displaceably on shaft 20. In one embodiment, shaft 20 has a guide rib 26 in the distal area, said rib having a T-shaped profile. The guide rib 26 is located centrally in the surface facing slide 22. Guide rib 26 extends in the axial direction. Slide 22 has on its distal end an axially extended guide groove 28 that is T-shaped in cross section. The guide groove 28 is located centrally in the side facing shaft 20. Guide groove 28 is open on the distal face of slide 22 so that slide 22 with its guide groove 28 can be slid onto guide rib 26 of shaft 20.

In the proximal portion of the slide 22, a guide rib 30 is formed on slide 22. This guide rib 30 is T-shaped in cross-section and extends axially along slide 22. The guide rib 30 is located centrally on the surface facing shaft 20. Guide rib 30 interdigitates with a guide groove of shaft 20. The guide groove of shaft 20 has a proximal section 32 positioned on the rearmost portion of the shaft 20, and a forward section 34 that forms the distal continuation of said guide groove. The proximal section 32 has a width that corresponds to the width of guide rib 30, so that this rib can be inserted freely into the proximal section 32 of the guide groove. In the forward section 34 the guide groove has a T-shaped cross-sectional profile that matches the cross-sectional profile of guide rib 30.

FIG. 1 shows slide 22 disposed proximally relative to shaft 20. In this proximal end position, guide rib 26 of shaft 20 is located anterior to the distal end of slide 22, and guide rib 30 of slide 22 is located within the wider proximal section section 32 of the guide groove of shaft 20. In this proximal end position, therefore, slide 22 can be lifted upward from shaft 20 or can be placed from above onto shaft 20. When slide 22 is pushed distally from this proximal end position shown in FIG. 1, the guide groove 28 on slide 22 slides onto guide rib 26 of shaft 20 and at the same time guide groove 30 on slide 22 slides into the T-shaped forward section 34 of guide groove of shaft 20.

Slide 22 has at its proximal end behind guide rib 30 a recess 36 that is open toward shaft 20, said recess being traversed by a cross pin 38. The second handle leg 12 projects with an end section 40 beyond articulation pin 16. This end section 40 passes into opening 14 in first handle leg 10 into recess 36 of slide 22. A transverse slot 42 is provided in end portion 40, said slot receiving cross pin 38, thus forming an articulation between this second handle leg 12 and slide 22. When the crosspin 38 on the slide 22 is engaged in the slot 42, a pivoting movement of second handle leg 12 relative to first handle leg 10 is thus converted into an axial displacement of slide 22 toward shaft 20.

In one embodiment, opening 14 of first handle leg 10 is so dimensioned that second handle leg 12 can be pivoted by means of spreading springs 18 into a maximally spread handle position as shown in FIG. 1. In this maximally spread position, second handle leg 12 comes in contact with the shaft-side edge of opening 14. In this maximally spread position, end section 40 of second handle leg 12 can come in contact with the handle-side edge of opening 14. In this maximally spread position, the endwise slot 42 of end section 40 of second handle leg 12 is inclined in the displacement direction of slide 22 to the point where the proximal edge 44 of slot 42 is located outside the path of movement of cross pin 38, while the distal edge 46 of slot 42 still projects into the path of movement of cross pin 38.

At the proximal rear side of first handle leg 10 a lock is mounted that includes a stop element that has the shape of a disk 48. Disk 48 is rotatable around a threaded bolt 50 inserted into handle leg 10. Disk 48 has on its circumference a flat edge 52 in the form of a separate segment. If disk 48 is turned so that its flat edge 52 adjoins opening 14, disk 48 is in its release position, as shown in this Figure. Because of flat edge 52, disk 48 does not project into opening 14 of first handle leg 10 and does not prevent the pivoting movement of second handle leg 12. A spring-loaded latching ball 56 mounted in first handle leg 10 engages latching recesses in the underside of disk 48 in order to allow the latter to engage in the release and locking positions.

In order to disassemble the sliding shaft instrument, disk 48 is rotated into the release position shown in FIG. 1. The second handle leg 12 is pivoted by means of spreading springs 18 into its maximally spread position. Now slide 22 can be slid into its proximal end position, as depicted in FIG. 1, since cross pin 38 can move beyond the proximal edge 44 of slot 42. In the position shown in FIG. 1, slide 22 can be lifted off shaft 20.

When the disk is in the release position shown in FIG. 1, the sliding shaft instrument previously disassembled can be reassembled. Slide 22 is placed on shaft 20 in the proximal end position shown in FIG. 1. Then slide 22 is slid distally, with guide groove 28 fitting over a guide rib 26 and guide rib 30 sliding from a rear section 32 of the guide groove into the forward section 34 of the guide groove. During the displacement of slide 22 in the distal direction, cross pin 38 slides over proximal edge 44 of slot 42 and into slot 42, coming to rest against the distal edge 46 of slot 42. During subsequent distal displacement, slide 22 carries second handle leg 12 with it over cross pin 38 and slot 42, so that the end section 40 is lifted off the proximal edge of opening 14. Once the slide 22 is engaged and the device reassembled, disk 48 can be turned into its locking position, as shown in more detail in FIGS. 3 and 4.

FIG. 2 shows a rear view of a sliding shaft instrument in the unlocked position with the slide removed. In this projection, the first handle leg 10 is visible, whereas the second handle leg is not visible. In this figure, the rotating disc 48 is shown with its flat edge 52 in the releasing position. The rotating disc 48 is held in place by a threaded bolt 50 around which the rotating disc 48 rotates. With the slide removed, the figure depicts the T-shaped forward section 34 of the guide groove on shaft 20, and the guide rib 26 of shaft 20.

FIG. 3 is a rear view of a sliding shaft instrument in the locked operating position. This figure shows the rotating disc 48 turned into a locking position. Rotating disc 48 is held in position by threaded bolt 50. Flat edge 52 is rotated away from the area where the two handle legs engage each other. In this projection, the first handle leg 10 is visible, and the second handle leg 12 is not. Disc 48 is turned with its curved edge 60 preventing the maximum spreading of the two handle legs. In this position, slide 20 cannot disengage.

Figure 4:
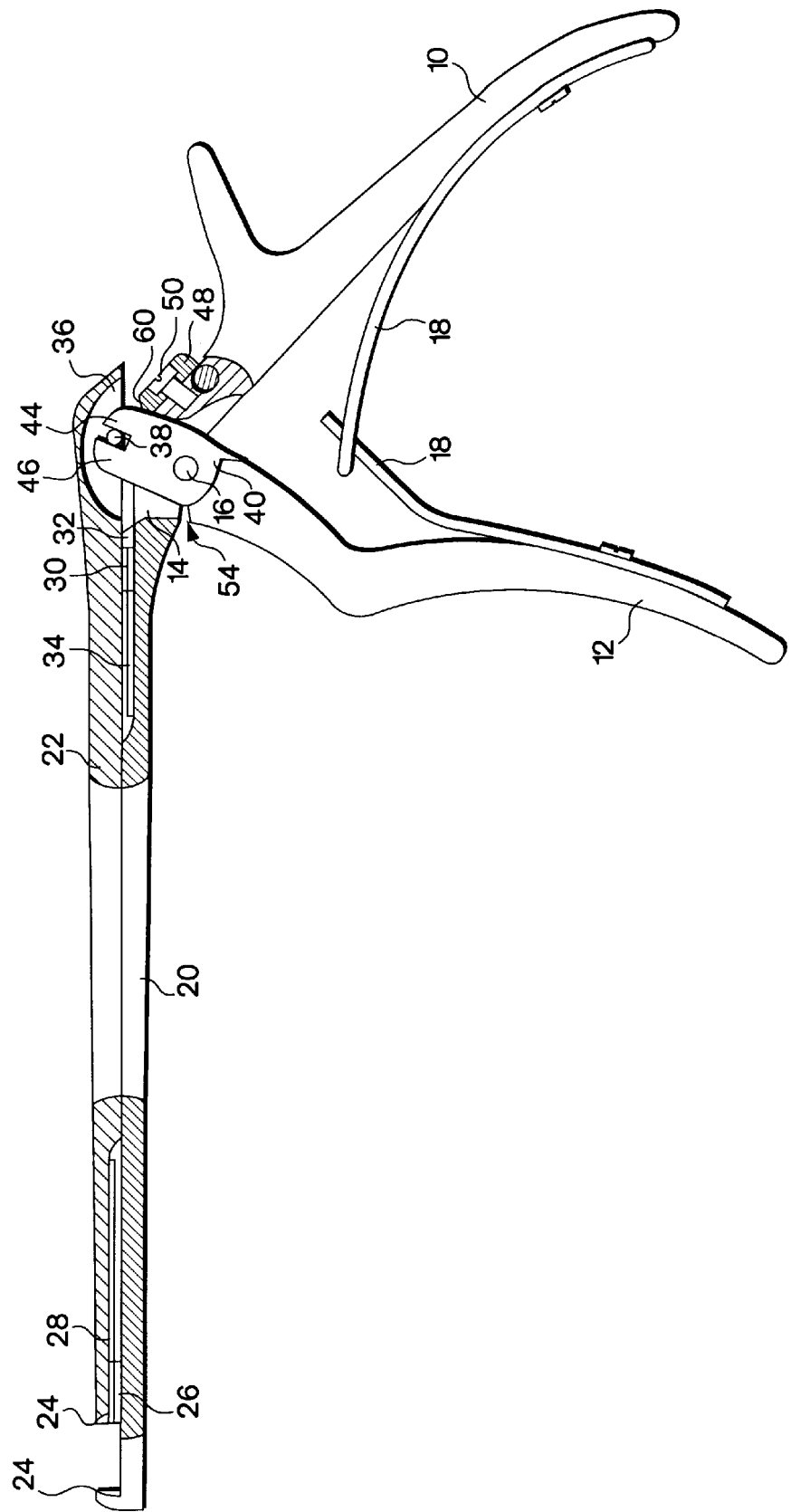
FIG. 4 shows a side view in partial axial section of the sliding shaft instrument in the locked operating position.

FIG. 4 shows a side view in partial axial section of an embodiment of a sliding shaft instrument illustrating the slide 22 in a locked position on the shaft 20. Disc 48 is shown in the locked position with its rounded edge 60 projecting into opening 14, thus limiting the pivoting movement of end section 40 and hence of second handle leg 12. The second handle leg 12 can therefore no longer reach its maximum spread position. In the handle position determined by the stop on disk 48 as shown in FIG. 2, slot 42 of end section 40 can tilt in the displacement direction of slide 22 only insofar as the proximal edge 44 of slot 42 does not enter the path of movement of cross pin 38. Cross pin 38 is thus received on both sides by slot 42 and cannot escape from slot 42. The interdigitation of slide 22 on shaft 20 by guide rib 26 and guide groove 28 distally and by guide rib 30 and forward section 34 of the guide groove cannot disengage.

It would be apparent to one of ordinary skill in the art that locking can also be accomplished with the same effect in a different manner. For example, instead of rotatably mounted disk 48, a linearly displaceable stop element can also be provided. Similarly, a rotatably or linearly displaceable stop element can engage this second handle leg 12 in front of articulation pin 16 to delimit the pivoting movement. As another example, a stop element could engage the gap 54 between second handle leg 12 and the shaft-side edge of opening 14 to produce the locking action. As a further example, a stop element can also be pivoted or slid into the sliding path of slide 22 in order to limit its displacement in the proximal direction.

While specific embodiments of the present invention have been disclosed and described, it will be understood by those skilled in the art that various changes in form and detail may be made without departing from the spirit and scope of the systems described herein. Accordingly, it will be understood that the invention is not to be limited to the embodiments disclosed herein, but is to be understood from the following claims, which are to be interpreted as broadly as allowed under the law.

What is claimed is:

1. Surgical instrument comprising:
   an elongate shaft member with no joints and having a distal end and a proximal end;
   a first handle leg connected to the proximal end of the shaft member;
   a second handle leg mounted pivotably relative to the first handle leg, wherein the second handle leg can be spread apart from or approximated to the first handle leg by pivoting said second handle leg on a pivot mechanism to the first handle leg, said pivot mechanism comprising an axially directed slot positioned in an end portion of the second handle leg and a cross pin capable of being received in the slot, wherein with maximal spreading of the first and the second handle legs the slot is inclined in a proximal displacement direction of a slide and the cross pin allows axial displacement of the slide into a fully retracted position on the proximal end of the shaft member;

said slide being axially displaceable on the shaft, and said slide being capable of being articulated with the second handle leg and capable of being removed from the shaft member when displaced to the fully retracted position on the proximal end of the shaft member;

a sliding path on the shaft member along which the axial displacement of the slide on the shaft member is guided; and a releasable lock capable of limiting pivoting of the second handle leg into a maximally spread position, wherein the releasable lock comprises a mechanical stop element.

2. Surgical instrument according to claim 1, wherein the cross pin can be pushed over the proximal edge of the slot in the end portion of the second handle leg when the second handle leg is in the maximally spread position.

3. Surgical instrument according to claim 1, wherein the mechanical stop element engages the pivoting path of the second handle leg, thereby obstructing the further motion of said second handle leg.

4. Surgical instrument according to claim 3, wherein the mechanical stop element is mounted pivotably on the first handle leg.

5. Surgical instrument according to claim 3, wherein the mechanical stop element is linearly displaceable on the first handle leg.

6. Surgical instrument according to claim 1, wherein the mechanical stop element engages the sliding path of the slide on the shaft member, thereby obstructing the further motion of said slide.

7. Surgical instrument according to claim 6, wherein the mechanical stop element is linearly displaceable on the shaft member.

8. Surgical instrument according to claim 1, wherein the releasable lock comprises the mechanical stop element, said mechanical stop element being capable of being locked by a latch.

9. Surgical instrument according to claim 1, wherein the first and second handle legs are capable of being spread and approximated by one hand.

10. Surgical instrument according to claim 1, wherein the first and second handle legs are spread by two hands.

11. Apparatus comprising:

an elongate shaft member having a distal end and a proximal end;

a slide capable of proximal and distal displacement along the elongate shaft member;

a slide path directed axially along the elongate shaft member into which the slide is inserted, wherein the proximal end of said slide path permits disengagement of the slide from the slide path;

a handle mechanism comprising a first and a second handle leg;

wherein the first handle leg is formed as a proximal extension of the elongate shaft member;

wherein the first handle leg is oriented at an angle to the longitudinal axis of the elongate shaft member;

wherein the second handle leg is mounted pivotably relative to the first handle leg;

wherein the second handle leg has a proximal and a distal end; and wherein the handle legs can be spread or approximated by the pivoting of the second handle leg upon the first handle leg;

a pivot mechanism comprising a slot directed axially in the proximal end of the second handle leg and a cross pin capable of being received in the slot, wherein with maximal spreading of the first and the second handle legs, the slot is inclined towards the proximal end of the elongate shaft member, and wherein the positioning of said slot permits axial displacement of the slide into its most proximal position on the proximal end of the elongate shaft member, thereby permitting the disengagement of the slide from the elongate shaft member; and a releasable lock capable of limiting the rotation of the second handle leg into a maximally spread position, wherein the releasable lock comprises a mechanical stop element.

12. Apparatus according to claim 11, wherein the cross pin is capable of being pushed over the proximal edge of the slot in the proximal end of the second handle leg when the second handle leg is in the maximally spread position.

13. Apparatus according to claim 11, wherein the mechanical stop element obtrudes into the pivoting path of the second handle leg, thereby obstructing the further motion of said second handle leg.

14. Apparatus according to claim 11, wherein the mechanical stop element obtrudes into the sliding path of the slide on the elongate shaft member, thereby obstructing the further motion of said slide.

15. Apparatus for use in general or minimally invasive or endoscopic surgery comprising:

an elongate shaft member having a proximal and a distal end;

a first handle leg affixed to the proximal end of the elongate shaft member;

a second handle leg capable of pivoting relative to the first handle leg and capable of being spread apart from the first handle leg or approximated thereto by the pivoting motion;

a slide path axially directed along the elongate shaft member, said slide path having a proximal and a distal end;

a slide capable of insertion into the slide path, whereby said slide can be directed proximally and distally along the elongate shaft member while remaining affixed thereto, and wherein the motion of the slide along the slide path is directed by the spreading and approximation of the second handle leg;

a slide engagement mechanism comprising a rib on the slide that is inserted into a groove on the slide path, and further comprising a cross pin on the slide that is inserted into a slot on the proximal end of the second handle leg;

a slide disengagement mechanism whereby with maximal proximal retraction of the slide on the elongate shaft, the rib on the slide is disarticulated from the groove on the slide path and whereby with maximal spreading of the handle legs, the slot in the proximal end of the second handle leg is directed towards the proximal end of the elongate shaft member, thereby permitting the disarticulation of the cross pin from the slot.

16. Apparatus for use in general or minimally invasive or endoscopic surgery comprising:

an elongate shaft member having a proximal and a distal end;

a first handle leg affixed to the proximal end of the elongate shaft member;

a second handle leg capable of pivoting relative to the first handle leg and capable of being spread apart from the first handle leg and approximated thereto by the pivoting motion;

a slide path axially directed along the elongate shaft member, said slide path having a proximal and a distal end;

a slide capable of insertion into the slide path, whereby said slide can be directed proximally and distally along the elongate shaft member while remaining affixed thereto, and wherein the motion of the slide along the slide path is directed by spreading and approximating the second handle leg;

a slide engagement mechanism comprising a rib inserted into a groove, thereby to engage the slide with the slide path, and further comprising a cross pin on the slide that is inserted into a slot on the proximal end of the second handle leg;

a slide disengagement mechanism whereby with maximal proximal retraction of the slide on the elongate shaft, the rib is disarticulated from the groove, thereby to disengage the slide from the slide path, and whereby with maximal spreading of the handle legs, the slot in the proximal end of the second handle leg is directed towards the proximal end of the elongate shaft member, thereby permitting disarticulation of the cross pin from the slot.

* * * * *